US007669482B2

(12) United States Patent
Jacobs et al.

(10) Patent No.: US 7,669,482 B2
(45) Date of Patent: Mar. 2, 2010

(54) SYSTEM AND METHOD FOR TESTING TUBULAR WELL PRODUCTS

(75) Inventors: Scott Jacobs, Edmonton (CA); Ahmed Hammami, Edmonton (CA); Todd Yakimoski, Beaumont (CA)

(73) Assignee: Schlumberger Technology Corporation, Sugar Land, TX (US)

( * ) Notice: Subject to any disclaimer, the term of this patent is extended or adjusted under 35 U.S.C. 154(b) by 216 days.

(21) Appl. No.: 11/864,406

(22) Filed: Sep. 28, 2007

(65) Prior Publication Data

US 2008/0164022 A1 Jul. 10, 2008

Related U.S. Application Data

(60) Provisional application No. 60/884,067, filed on Jan. 9, 2007.

(51) Int. Cl.
*G01N 3/24* (2006.01)
(52) U.S. Cl. ......................................................... 73/841
(58) Field of Classification Search .................. 73/857, 73/841, 581, 622, 795, 796; 285/38; 294/94
See application file for complete search history.

(56) References Cited

U.S. PATENT DOCUMENTS

| 5,068,800 | A | * | 11/1991 | Brook et al. ................... 702/36 |
| 5,799,985 | A | * | 9/1998 | Murphy ........................ 285/38 |
| 6,435,582 | B1 | * | 8/2002 | DaSilva et al. ................. 294/94 |
| 2004/0091076 | A1 | * | 5/2004 | Kerr et al. .................... 376/260 |
| 2008/0053239 | A1 | * | 3/2008 | Tunney ......................... 73/857 |

OTHER PUBLICATIONS

Busser, G.C., "Selection Criteria on Oilfield Tubulars"; 7th NACE International Middle East Corrosion Conf. Proceeding V1, pp. 418 to 428, Manama, Bahrain, Feb. 26-28, 1996.
Dusseault, M.B. et al., "Casing Shear: Causes, Cases, Cures"; SPE Drilling & Completion, pp. 98-107, Jun. 2001, SPE 72060.
Evans, G.W. and Harriman, D.W.: "Laboratory Test on Collapse Resistance of Cemented Casing", Proceedings of 47th Annual Fall Meeting of the Society of Petroleum Engineers of AIME, San Antonio, Texas, Oct. 8-11, 1972.
Fredrich, J.T. et al., "Three-Dimensional Geomechanical Simulation of Reservoir Compaction and Implications for Well Failures in the Belridge Diatomite", 1996 SPE Annual Technical Conference and Exhibition, Denver, Colorado, Oct. 6-9, 1996, SPE 36698.
He, L. et al., "Challenges and Countermeasures Facing Casing Damage in Daqing Oilfield", 2005 SPE Europe/EAGE Annual Conference, Madrid, Spain, Jun. 13-16, 2005, SPE 92292.
Hilbert, L.B. Jr. et al., "Field-Scale and Wellbore Modeling of Compaction-Induced Casing Failures", SPE Drilling & Completion 14(2), pp. 92-1001, Jun. 1999.
Ravi, K. et al., "A Comparative Study of Mechanical Properties of Density-Reduced Cement Compositions", SPE 90068, 2004.

* cited by examiner

*Primary Examiner*—Jewel Thompson
(74) *Attorney, Agent, or Firm*—Robert A. Van Someren; Wayne I. Kanak

(57) ABSTRACT

A technique enables testing of a wellbore tubular under simulated well conditions. The wellbore tubular is mounted in a fixture for testing. Controllable systems are used to subject the wellbore tubular to a variety of predetermined conditions simulating potential downhole environments. The controllable systems include manipulators able to place the wellbore tubular under predetermined load, displacement, temperature, and pressure conditions.

25 Claims, 4 Drawing Sheets

SYSTEM AND METHOD FOR TESTING TUBULAR WELL PRODUCTS

CROSS-REFERENCE TO RELATED APPLICATIONS

This application claims priority to U.S. Provisional Application No. 60/884,067, filed Jan. 9, 2007. This application is related to U.S. Provisional Application No. 60/884,075, also filed Jan. 9, 2007, and to the regular patent application filed of even date herewith claiming priority therefrom.

BACKGROUND OF THE INVENTION

In many downhole applications, various tubular products and tubular product materials are used in well-related applications. The tubular well products are deployed into wellbores drilled into the earth through reservoirs that contain production fluid, such as oil or gas. In some oilfield environments, the tubular well products are subjected to stresses that can have a detrimental effect on the well products. The stresses can be caused by zonal slip, reservoir compaction, gravel pack packers, liner overlap, cement voids, thermal gradients, and other well conditions that can lead to tubular ovalisation and other detrimental effects, and can result in catastrophic failure.

For example, reservoir compaction can be severe enough to cause failure of the tubular well product through tension, buckling, collapse, and/or shearing. In some environments, shear loading causes severe localized deformation of the tubular well product, e.g. deformation of well casing. Some subsurface shale regions, for example, are prone to shift horizontally as reservoirs undergo vertical compaction or subsidence. The shifting of the reservoir can place a variety of tubular well products under high loads that ultimately lead to damage or failure of the well product. Depending on the reservoir, the loads potentially experienced by the well product can be directed in a variety of orientations, e.g. axially or in shear. However, no suitable approach exists for preliminary testing of the various tubular well products to adequately determine the reaction to such loads.

BRIEF SUMMARY OF THE INVENTION

In general, the present invention provides a system and method for evaluating a wellbore tubular member under simulated well conditions. The evaluation is accomplished by mounting the wellbore tubular to a fixture and subjecting the wellbore tubular to a variety of predetermined conditions simulating potential downhole environments. The ability to pretest a variety of tubular well products facilitates the design and construction of components and systems better able to withstand challenging environmental conditions when placed into operation in a wellbore.

BRIEF DESCRIPTION OF THE DRAWINGS

Certain embodiments of the invention will hereafter be described with reference to the accompanying drawings, wherein like reference numerals denote like elements, and.

DETAILED DESCRIPTION OF THE INVENTION

In the following description, numerous details are set forth to provide an understanding of the present invention. However, it will be understood by those of ordinary skill in the art that the present invention may be practiced without these details and that numerous variations or modifications from the described embodiments may be possible.

The present invention generally relates to a system and methodology for evaluating tubulars used in well-related applications, such as hydrocarbon production applications. Various wellbore tubulars, e.g. completions system tubulars, can be evaluated prior to deployment into a wellbore to mitigate detrimental effects on the tubular components during use in the wellbore environment. The ability to pretest or pre-evaluate the tubular system or component design helps to, for example, mitigate component ovalisation and shear failures that can result from stresses induced by zonal slip, reservoir compaction/subsidence, gravel pack packers, liner overlap, cement voids, thermal gradients, and other reservoir-related conditions.

By way of example, the present system and methodology can be used to test many types of well-related tubular product designs and materials used in constructing the tubular product. Equipment used in oilfield applications can include tubular tool housings, sample cylinders, coiled tubing, drill collars, liners, casing, and other components utilized in a downhole environment. Additionally, the material used to create the tubular components or portions of the tubular components can readily be tested against simulated conditions to which such components may be exposed in the downhole environment. For example, the use of fiber-reinforced materials, such as fiber-reinforced plastic, or other composite materials, can readily be tested in a variety of tubular component types. This is particularly helpful in testing materials for which the mechanical properties have not been well defined and which may exhibit a complex response.

The tubular component design can be tested by applying predetermined loads, either as independent loads or as combined loads, displacements, and/or rotations to test specimens. For example, independent or combined shear and axial loads can be applied. Depending on the specific well environment anticipated, the product can be tested under tension, compression, torsion, shear, and combinations of these loads. In some embodiments, additional thermal, pressure, and environmental conditions can be added to the test regimen to determine the capabilities of a particular wellbore tubular at downhole conditions. Generally, the system and methodology can be used to simulate a downhole environment, including various formation movements that have been known to cause buckling of tubular components, such as casing.

Figure 1:
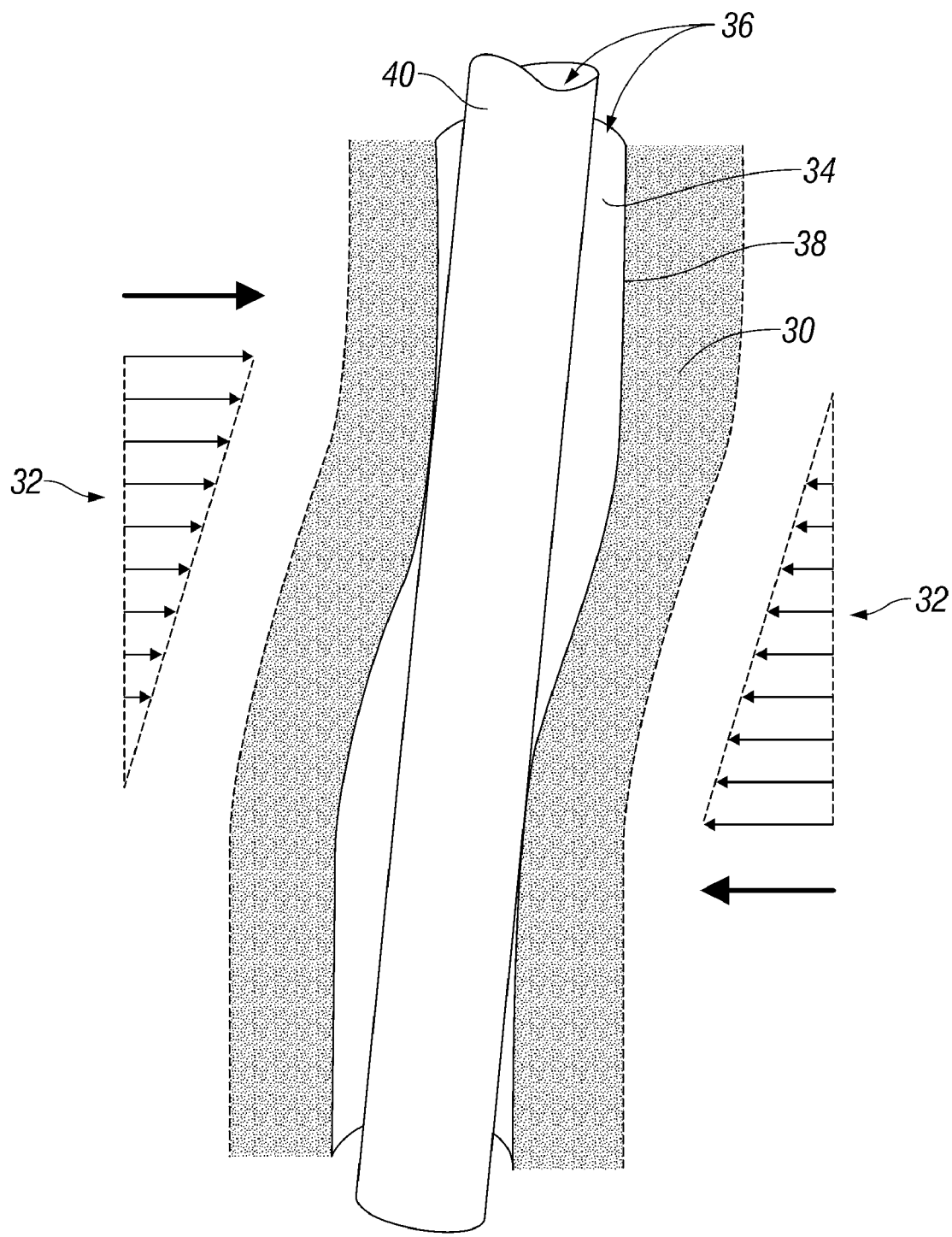
FIG. 1 is a front elevation view of a wellbore tubular under shear loading, according to an embodiment of the present invention.

In various well environments, downhole tubular components, e.g. completion system components, are subjected to substantial shear forces. The shear forces are caused by, for example, displacement of rock strata along bedding planes and along inclined fault planes. As illustrated in FIG. 1, a shifting reservoir material 30, resulting from displacement of the rock strata or other environmental change, can create a displacement field 32 able to distort a wellbore 34. If the forces creating displacement field 32 are sufficiently strong, the distortion of wellbore 34 can detrimentally affect tubular components 36 deployed within the wellbore 34. Tubular components 36, such as a well casing 38 or completion system tubular 40, can suffer detrimental effects or even failure, particularly when the shear forces are applied over a relatively short distance. The damaging displacement field 32 can be established at many reservoir related regions, such as weak lithology interfaces within the overburden, that create localized horizontal shear. Other regions that can experience damaging localized horizontal shear include the upper portion of production and injection intervals, as well as regions proximate casing perforations.

Figure 2:
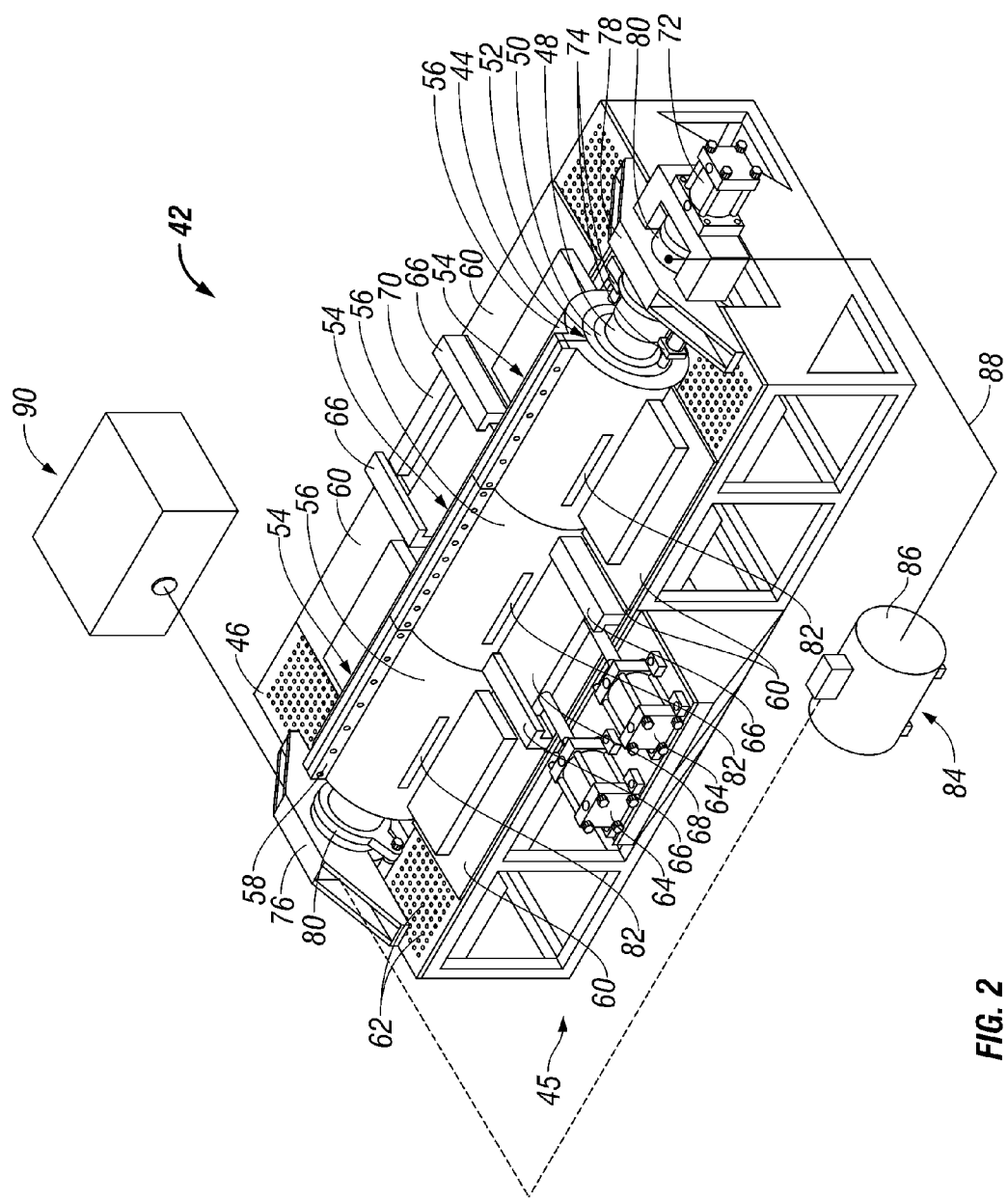
FIG. 2 is an orthogonal view of a wellbore tubular positioned in a testing system, according to an embodiment of the present invention.

Referring generally to FIG. 2, one example of a system 42 for testing, wellbore tubulars is illustrated. In this embodiment, a wellbore tubular 44, such as a completion system tubular, is placed in a fixture 45 designed to induce simulated loading scenarios that the wellbore tubular 44 may experience in a well environment. The fixture 45 can also be used to simulate a variety of other well-related conditions related to, for example, temperature and pressure. As illustrated, the wellbore tubular 44 is mounted on a framework 46 that serves as a test frame for testing wellbore tubular 44 under the simulated well conditions. The wellbore tubular 44 may comprise many different types of tubular components utilized in downhole environments. Additionally, the wellbore tubular 44 may comprise single or multiple material layers depending on the goals of the evaluation. For example, wellbore tubular 44 may comprise a casing or completion system tubular 48 surrounded by a cement material layer 50 which, in turn, is surrounded by a formation rock layer 52. Use of the cement material layer and formation rock layer facilitates evaluation of the effects of force loads and/or displacements potentially experienced in the downhole environment.

The wellbore tubular 44 is mounted to framework 46 by a plurality of clamping mechanisms 54, at least one of which is movable to enable application of shear loads. By way of example, each clamping mechanism 54 may comprise a clamshell 56 having arcuate shells that can be opened to receive wellbore tubular 44. The clamshells 56 are then closed around the wellbore tubular 44 and secured by an appropriate closure mechanism 58 during the test procedures. The clamping mechanisms 54 may be mounted to framework 46 by mounting plates 60. In some embodiments, the clamping mechanisms are mounted at various locations along framework 46. For example, framework 46 may comprise a grid of mounting holes 62 that enable the secure fastening of mounting plates 60 at a variety of locations via appropriate fasteners, such as threaded fasteners.

During evaluation, predetermined shear loads and axial loads can be applied to wellbore tubular 44 via a plurality of manipulation mechanisms. For example, one or more manipulation mechanisms 64 can be mounted to framework 46 to apply transverse or shear loads to wellbore tubular 44. In the embodiment illustrated, the central clamping mechanism 54 is movable while the other clamping mechanism or mechanisms remains stationary. The manipulation mechanisms 64 are oriented to act against the movable central clamping mechanism 54 and to apply either a predetermined force against the movable central clamping mechanism 54 or a predetermined displacement of movable central clamping mechanism 54. The action of manipulation mechanisms 64 enables evaluation of wellbore tubular 44 under a variety of shear loads, including double shear loads and single shear loads. For example, the movable central clamping mechanism 54 may be positioned between two stationary clamping mechanisms 54 to induce a double shear. The wellbore tubular 44 can also be evaluated under a single shear load simply by removing one of the stationary clamping mechanisms 54.

In the embodiment illustrated, the movable central clamping mechanism 54 is constrained against vertical movement by a plurality of runners 66 that slidably receive a movable plate 68 formed as part of the movable central clamping mechanism 54. Additionally, horizontal movement during inducement of the shear loading is limited by a stop 70. Stop 70 can be an adjustable stop mountable at different positions on framework 46 to allow for the selection of different maximum displacements of wellbore tubular 44. The geometry of framework 46 accommodates a range of system sizes as well as a range of wellbore tubular specimen diameters and lengths. The grid of mounting holes 62 further accommodates numerous loading configurations and enables the use of several sizes of clamping mechanisms 54, e.g. clamshells having a range of diameters and/or lengths.

The wellbore tubular 44 can also be placed under various axial loads via a plurality of manipulation mechanisms 72, 74. In the embodiment illustrated, wellbore tubular 44 is mounted to end restraints 76 and 78 via adapter collars 80 that are affixed to wellbore tubular 44 at its axial ends. At least one of the end restraints 76, 78 is movable to enable application of axial loads. By way of example, end restraint 76 may be fixed to framework 46, and end restraint 78 may be movable under the influence of manipulation mechanisms 72 and 74. Accordingly, manipulation mechanism 72 can be selectively actuated to move end restraint 78 and apply compressive axial loads to the wellbore tubular 44. Similarly, manipulation mechanisms 74 can be selectively actuated to move end restraint 78 in an opposite direction for applying tensile axial loads to the wellbore tubular 44. In the specific example illustrated, the axial loading is applied directly to the casing/completion system tubular 48; however the axial loading can be applied to the entire axial end of wellbore tubular 44 or to portions thereof depending on the desired evaluation. It should be noted that additional or alternate manipulation mechanisms 74 can be oriented to apply twisting or torsional loads to the wellbore tubular 44 through adapter collar 80. Additionally, the manipulation mechanisms 64, 72, 74 can be constructed in a variety of forms depending on, for example, the structure of clamping mechanisms 54 and adapter collars 80. By way of example, manipulation mechanisms 64, 72, 74 are linear actuators, such as hydraulic cylinders or solenoids.

The wellbore tubular 44 also can be subjected to a variety of other simulated well conditions. For example, a temperature control system can utilize heating elements 82 deployed along wellbore tubular 44 to enable temperature control with respect to the wellbore tubular 44. The elements 82 allow the selected heating and/or cooling of wellbore tubular 44 to better simulate conditions in a downhole wellbore environment. In the embodiment illustrated, heating elements 82 are positioned within clamping mechanisms 54. However, the heating elements can be mounted directly to wellbore tubular 44, or the temperature control can be provided by alternate methods, including liquid circulation and Peltier devices. Some of these devices can be used to selectively cool the wellbore tubular 44. Furthermore, insulated covers or blankets also can be installed over wellbore tubular 44 to contain or repel heat.

System 42 may also comprise a pressure control system 84 to enable the selective application of pressure against wellbore tubular 44. For example, a pump 86 may be coupled to an appropriate port of adapter collar 80 via a pressure line 88.

The adapter collar 80 is sealingly engaged with the end of wellbore tubular 44 to enable the pressurization of wellbore tubular 44. In the embodiment illustrated, pressure is applied internally, however pressure control system 84 can also be utilized in applying an external pressure to wellbore tubular 44 or to apply pressure between layers of the wellbore tubular, e.g. between concentric tubular members.

In the embodiment illustrated, temperature control system, pressure control system 84, and manipulation mechanisms 64, 72, 74 are controlled by a suitable control system 90, such as a computer-based control system. For example, control system 90 can be programmed to provide the wellbore tubular 44 with one or more evaluation regimens in which predetermined loads, temperatures, and/or pressures are applied to wellbore tubular 44. By way of example, the loads applied to wellbore tubular 44, e.g. shear loads and axial loads, can be applied sequentially or in combination.

Figure 3:
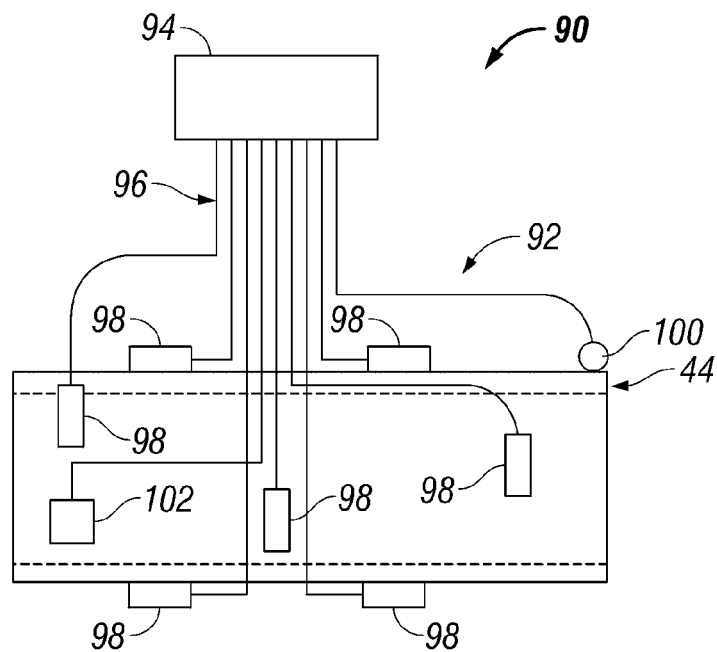
FIG. 3 is a schematic illustration of a sensor and control system that can be used as part of the testing system illustrated in FIG. 2, according to an embodiment of the present invention.

In some embodiments, control system 90 also comprises a feedback system 92 that provides data on the effects or results of the test procedures on wellbore tubular 44, as illustrated in FIG. 3. The feedback system 92 may comprise a variety of sensors connected to an automated control 94 via a plurality of communication lines 96. Communication lines 96 can comprise physical lines and/or wireless lines. In the embodiment illustrated, feedback system 92 comprises a plurality of strain sensors 98 positioned to sense the strain induced in wellbore tubular 44 during application of, for example, shear loads, axial loads, and torsional loads. The feedback system 92 may also comprise a variety of other sensors, such as temperature sensors 100 and pressure sensors 102. Data from the various sensors is fed back to automated control 94 for evaluation of the wellbore tubular 44 during and following testing of the wellbore tubular 44 under simulated well conditions. By way of example, fixture 45 can be instrumented to measure tensile force, compressive force, torsion force, axial deflection, transverse deflection, angular deflection, strain of various components tested, bore pressure, annulus pressure, external pressure, and temperature.

Figure 4:
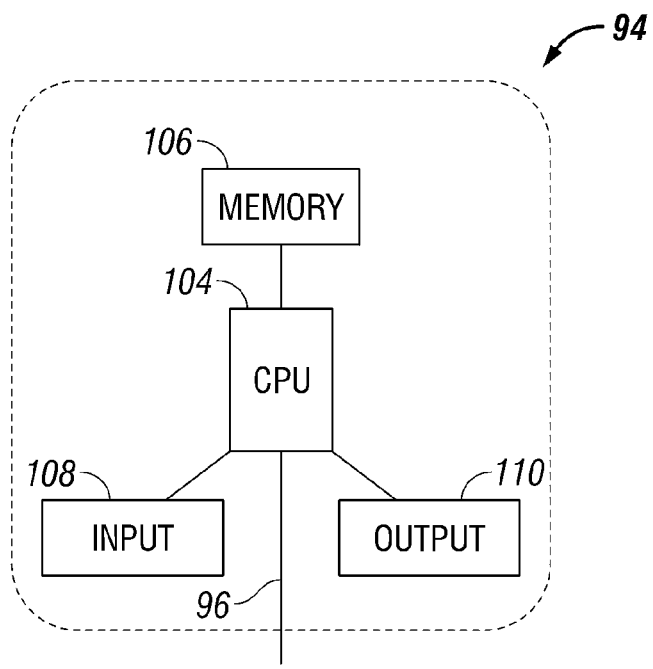
FIG. 4 is a schematic illustration of the control system illustrated in FIG. 3, according to an embodiment of the present invention.

The automated control 94 of control system 90 may comprise a computer-based system having a central processing unit (CPU) 104, as illustrated in FIG. 4. CPU 104 may be operatively coupled to a memory 106, as well as an input device 108, and an output device 110. Additionally, CPU 104 may be operatively coupled with the various test control systems, including temperature elements 82, pressure control system 84, and manipulation mechanisms 64, 72 and 74. In some applications, the data provided by feedback system 92 is utilized by automated control 94 in adjusting the input provided by the various test control systems. In the embodiment illustrated, input device 108 may comprise a variety of devices, such as a keyboard, mouse, voice-recognition unit, touchscreen, other input devices, or combinations of such devices. Output device 110 may comprise a visual and/or audio output device, such as a monitor having a graphical user interface. Additionally, the processing of data and control functions may be done on a single device or multiple devices located proximate fixture 45, away from fixture 45, or with some devices located proximate fixture 45 and other devices located remotely.

Figure 5:
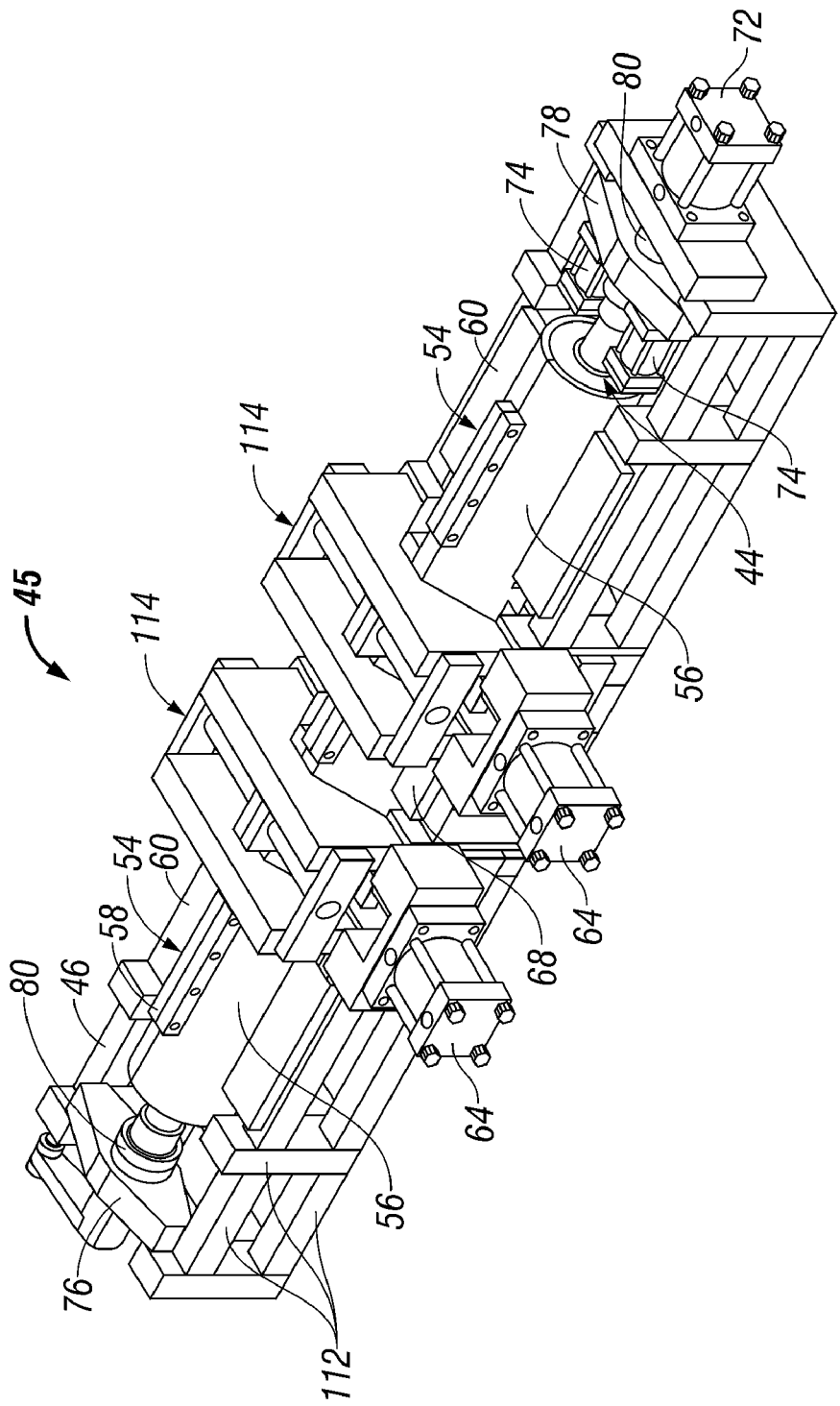
FIG. 5 is another embodiment of the wellbore tubular testing system, according to an alternate embodiment of the present invention.

Referring generally to FIG. 5, an alternate embodiment of fixture 45 is illustrated. In this embodiment, framework 46 is reinforced to allow a higher loading capacity during testing of wellbore tubular 44. For example, a plurality of stronger frame struts 112 are joined to withstand the higher loads exerted by manipulation mechanisms 64, 72 and 74. Additionally, a plurality of crossover braces 114 are connected across the clamping mechanisms 54 proximate manipulation mechanisms 64 to counter the increased forces exerted by manipulation mechanisms 64. Otherwise, the function of the various manipulation mechanisms, clamping mechanisms, temperature system, pressure system, and sensors is similar to that described above with reference to the embodiment of FIG. 2.

The system 42 provides an operator with the ability to perform a wide range of concept testing on tubular product designs intended for oilfield use. By way of example, the system enables validation of mechanical properties for materials under consideration. Additionally, system 42 is sufficiently flexible to screen a variety of tubular product design concepts related to housings, coiled tubing, cylinders, casing, and other wellbore tubulars and to provide substantial data on operation of such components under harsh wellbore conditions. The system 42 also can be used to validate predictive models for tubular components or systems.

During testing, system 42 is able to emulate loading conditions on the wellbore tubular representative of those expected downhole due to deployment and/or formation interaction. The loading conditions can comprise tension, compression, shear, torsion, pressure, temperature and various combinations of these parameters that affect the tubular component or system. Additionally, the results of the evaluation can be scaled so that testing can be performed on smaller diameter wellbore tubulars. However, fixture 45 is readily adaptable to accommodate a wide range of wellbore tubular sizes.

The structure of framework 46 can be adjusted according to the loads applied during testing. Additionally, the type, size and location of the various manipulation mechanisms can be changed to apply desired axial loads, shear loads, torsional loads, other loads and combinations of loads against the wellbore tubular 44. The control system 90 can also be adjusted according to the components controlled and according to the instrumentation utilized in evaluating the effects on the wellbore tubular 44. Furthermore, the size, structure, and material used to construct clamping mechanisms 54 can be adjusted according to the size and material of the wellbore tubular 44, e.g. wellbore component or wellbore system, subject to evaluation.

Accordingly, although only a few embodiments of the present invention have been described in detail above, those of ordinary skill in the art will readily appreciate that many modifications are possible without materially departing from the teachings of this invention. Such modifications are intended to be included within the scope of this invention as defined in the claims.

What is claimed is:

1. A method of evaluating a completion system tubular, comprising:
    mounting a completion system tubular on a test framework having a plurality of manipulation mechanisms;
    operating at least one manipulation mechanism of the plurality of manipulation mechanisms to place a shear load on the completion system tubular for evaluation of the completion system tubular under predetermined shear load conditions; and
    actuating another manipulation mechanism of the plurality of manipulation mechanisms to place an axial load on the completion system tubular for evaluation of the completion system tubular under predetermined axial load conditions.

2. The method as recited in claim 1, further comprising actuating another manipulation mechanism of the plurality of manipulation mechanisms to place a torsional load on the completion system tubular for evaluation of the completion system tubular under predetermined torsional load conditions.

3. The method as recited in claim 1, wherein operating at least one manipulation mechanism comprises placing a single shear load on the completion system tubular.

4. The method as recited in claim 1, wherein operating at least one manipulation mechanism comprises placing a double shear load on the completion system tubular.

5. The method as recited in claim 1, wherein actuating another manipulation mechanism comprises placing a tensile load on the completion system tubular.

6. The method as recited in claim 1, wherein actuating another manipulation mechanism comprises placing a compressive load on the completion system tubular.

7. The method as recited in claim 1, wherein mounting the completion system tubular comprises holding the completion system tubular with a plurality of arcuate mounts, at least one of the arcuate mounts being movable to induce the shear load.

8. The method as recited in claim 2, further comprising sensing reaction of the completion system tubular to the shear load, the axial load, and the torsional load; and providing data on the reaction to a control system for evaluation.

9. The method as recited in claim 1, wherein mounting comprises mounting a fiber reinforced tubular on the test framework.

10. The method as recited in claim 1, wherein mounting the completion system tubular comprises mounting a casing tubular surrounded by cement and/or formation rock on the test framework.

11. The method as recited in claim 1, further comprising increasing the temperature of the completion system tubular while on the test framework.

12. The method as recited in claim 11, further comprising increasing pressure acting on the completion system tubular while on the test framework.

13. A system for testing completion system components, comprising:
 a framework;
 a plurality of clamping mechanisms selectively closable around a completion system component;
 an axial manipulator coupled to the completion system component through an adapter collar; and
 a shear manipulator coupled to a movable clamping mechanism of the plurality of clamping mechanisms, the axial manipulator and the shear manipulator being controllable to test the completion system component under axial and shear loads.

14. The system as recited in claim 13, further comprising a torsional manipulator coupled to the completion system component, the torsional manipulator being controllable to test the completion system component under torsional loads.

15. The system as recited in claim 13, further comprising a heating element to heat the completion system component during testing.

16. The system as recited in claim 15, further comprising a pressure system to selectively expose the completion system component to pressure during testing.

17. The system as recited in claim 13, further comprising a sensor system to measure reaction of the completion system component during testing.

18. A method, comprising:
 mounting a wellbore tubular in a fixture; and
 testing the wellbore tubular under simulated well conditions by controlling the fixture to subject the wellbore tubular to predetermined conditions of shear load, axial load and temperature.

19. The method as recited in claim 18, further comprising controlling the fixture to subject the wellbore tubular to predetermined conditions of torsional load.

20. The method as recited in claim 18, wherein testing further comprises using the fixture to subject the wellbore tubular to predetermined pressure conditions.

21. The method as recited in claim 18, wherein mounting the wellbore tubular comprises gripping the wellbore tubular with clamping mechanisms sized to encircle and clamp a completion tubular surrounded by a cement layer.

22. The method as recited in claim 18, wherein testing comprises subjecting the wellbore tubular to a double shear load.

23. The method as recited in claim 18, further comprising actuating a plurality of Linear actuators to apply shear load and axial load.

24. A system, comprising:
 a clamping mechanism to selectively secure a wellbore tubular for testing;
 a plurality of mechanical actuators positioned to act against the wellbore tubular when held by the clamping mechanism; and
 a control system to adjust the actuators, the actuators being sufficiently adjustable to simulate a variety of wellbore Load conditions potentially acting against the wellbore tubular.

25. The system as recited in claim 24, further comprising a temperature system to control the temperature of the wellbore tubular.

* * * * *